United States Patent
Fukuda et al.

(10) Patent No.: US 7,595,400 B2
(45) Date of Patent: Sep. 29, 2009

(54) PROCESS FOR THE PREPARATION OF HEXACYCLIC COMPOUNDS

(75) Inventors: Hiroshi Fukuda, Kanagawa (JP); Takeshi Murata, Kanagawa (JP); Satoshi Niizuma, Kanagawa (JP); Hitomi Suda, Kanagawa (JP); Masao Tsukazaki, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 655 days.

(21) Appl. No.: 10/546,287

(22) PCT Filed: Feb. 20, 2004

(86) PCT No.: PCT/JP2004/002023

§ 371 (c)(1),
(2), (4) Date: Mar. 20, 2006

(87) PCT Pub. No.: WO2004/073601

PCT Pub. Date: Sep. 2, 2004

(65) Prior Publication Data

US 2006/0178376 A1    Aug. 10, 2006

(30) Foreign Application Priority Data

Feb. 21, 2003   (EP) ................. 03003232

(51) Int. Cl.
C07D 239/00  (2006.01)
C07D 239/70  (2006.01)
C07D 239/72  (2006.01)
C07D 471/00  (2006.01)
C07D 487/00  (2006.01)
C07D 491/00  (2006.01)
C07D 498/00  (2006.01)
C07D 515/00  (2006.01)

(52) U.S. Cl. .................. 544/245; 544/283; 546/89
(58) Field of Classification Search ................ 544/245, 544/283; 546/89
See application file for complete search history.

(56) References Cited

U.S. PATENT DOCUMENTS

2003/0138864 A1 *   7/2003   Ishitsuka et al. ......... 435/7.23

FOREIGN PATENT DOCUMENTS

| EP | 0220601 | 5/1987 |
|---|---|---|
| EP | 0296597 | 12/1988 |
| EP | 0495432 | 7/1992 |
| EP | 0897924 | 2/1999 |
| WO | WO 90/03169 | 4/1990 |
| WO | WO 03/045952 | 6/2003 |

OTHER PUBLICATIONS

Gelderblom et al., "Oral Topoisomerase 1 inhibitors in adult patients:" Invest. New Drugs 17:401-415, 1999.
Gerrits et al., "Topoisomerase 1 inhibitors: the relevance of prolonged . . . " Brit. J. of Cancer 76(7):952-962, 1997.
Hatefi et al., "Camptothecin Delivery Methods" Pharm. Res. 19(10):1389-1399, 2002.
Kehrer et al., "Modulation of camptothecin analogs in the treatment of cancer: a review" Anti-Cancer Drugs 12:89-105, 2001.
Kingsbury et al., "Synthesis of Water-Soluble (Aminoalkyl) camptothecin Analogues:" J. Med. Chem. 34:98-107, 1991.
Kunimoto et al., "Antitumor Activity of 7-Ethyl-10-[4-(1-piperidino)-1-piperidino]carbonyloxy-camptothecin," Cancer Res. 47:5944-5947, 1987.
O'Leary et al., "Camptothecins: a Review of their Development and Schedules of Administration" Eur. J. of Cancer 34(10):1500-1508, 1998.
Sugimori et al., "Antitumor Agents. VI. Synthesis and Antitumor Activity of Ring A-, Ring B-, and Ring C-Modified . . . " Heterocycles 38(1):81-94, 1994.
Sugimori et al., "Synthesis and Antitumor Activity of Ring A- and F-Modified Hexacyclic Camptothecin Analogues" J. Med. Chem. 41:2308-2318, 1998.
Zunino et al., "Camptothecins in clinical development" Expert Opin. Investig. Drugs 13(3):269-284, 2004.

* cited by examiner

Primary Examiner—James O Wilson
Assistant Examiner—Erich A Leeser
(74) Attorney, Agent, or Firm—Fish & Richardson P.C.

(57) ABSTRACT

This invention relates to novel processes for the preparation of compounds of the formula [1], wherein R1, R2, R3 and R4 are as defined in the claims and description as well as pharmaceutically acceptable salts thereof. The compounds of the formula [1] are hexacyclic compounds having potent antitumor activity.

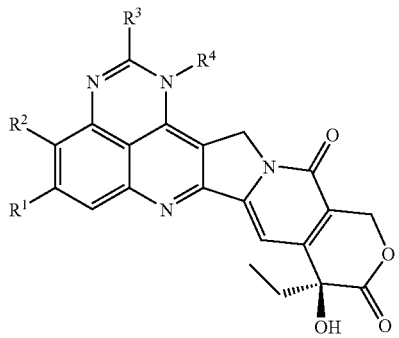

[1]

5 Claims, No Drawings

PROCESS FOR THE PREPARATION OF HEXACYCLIC COMPOUNDS

CROSS-REFERENCE TO RELATED APPLICATIONS

This application is the National Stage of International Application No. PCT/JP2004/002023, filed Feb. 20, 2004, which claims the benefit of European Patent Application Serial No. 03003232.0, filed on Feb. 21, 2003. The contents of both applications are hereby incorporated by reference in their entireties.

TECHNICAL FIELD

The present invention relates to a novel process for the preparation of novel hexacyclic compounds (camptothecin analogs) having potent anti-tumor activity.

BACKGROUND ART

The cytotoxic activity of camptothecin is attributable to its ability to interfere with DNA topoisomerase I (Hsiang, Y.-H. et al. Camptothecin induces protein-linked DNA breaks via mammalian DNA topoisomerase I. J. Biol. Chem., 260: 14873-14878, 1985). DNA topoisomerase I is a phosphorylated protein and is required for DNA replication, transcription and recombination. It forms a covalent reversible DNA topoisomerase I-double strand DNA complex (referred to as cleavable complex) and relaxes supercoiled DNA by cleaving and religating one of the two DNA strands (see for example Wang, J. C. DNA topoisomerases. Annu. Rev. Biochem. 54:665-697, 1985; Champoux, J. J. Mechanistic aspects of type-I topoisomerase. In "DNA topology and its biological effects" pp. 217-242, 1990). Camptothecin reversibly interacts with the cleavable complex and subsequently induces DNA single strand breaks by interfering with the religation step (Hsiang, Y.-H. et al. Camptothecin induces protein-linked DNA breaks via mammalian DNA topoisomerase I. J. Biol. Chem., 260:14873-14878, 1985; Porter, S. E. et al. The basis for camptothecin enhancement of DNA breakage by eukaryotic DNA topoisomerase I. Nucleic Acid Res. 17:8521-8532, 1989).

Although DNA topoisomerase I is an ubiquitous enzyme and is present throughout the cell cycle, antiproliferative activities of camptothecin are only limited in clinical trials, and half-life in plasma of camptothecin appeared to be short (less than 30 min) being converted to the inactive carboxylate form. Furthermore, camptothecin is poorly soluble in water, and therefore, it itself can not be formulated for the use of intravenous injection.

A number of camptothecin derivatives were synthesized to improve anti-tumor activity, lactone stability in plasma and/or water solubility, and were tested clinically (Gerrits, C. J. H., de Jonge, M. J. et al. Topoisomerase I inhibitors: the relevance of prolonged exposure for clinical development. Br. J. Cancer, 76: 952-962, 1997; O'Leary, J. et al. Camptothecins: a review of their development and schedules of administration. Eur. J. Cancer, 34: 1500-1508, 1988; Gerderblom, H. A. et al. Oral topoisomerase I inhibitors in adults patients: present and future. Investig. New Drugs, 17: 401-415, 1999).

However, at the present time, only two camptothecin derivatives, 7-ethyl-10-[4-(1-piperidino)-1-piperidino]carbonyloxycamptothecin(irinotecan) that is the prodrug of 7-ethyl-10-hydroxycamptothecin (SN-38, EP 0074256) and 9-(dimethylamino)methyl-10-hydroxycamptothecin(topotecan) have been introduced into clinical practice (Kunimoto, T. et al. Antitumor activity of 7-ethyl-10-[4-(1-piperidino)-1-piperidino]carbonyloxycamptothecin, a novel water-soluble derivative of camptothecin, against murine tumors. Cancer Res., 47:5944-5947, 1987; Kingsbury, W. D. et al. Synthesis of water-soluble (aminoalkyl)camptothecin analogs: inhibition of topoisomerase I and antitumor activity. J. Med. Chem., 34:98-107, 1991).

Due to the structural complexity of camptothecin, there is clearly a limitation of derivatization of camptothecin and synthetic routes preparing them. Thus, there are still strong needs to discover new synthetic routes for delivering new camptothecin analogs with improved activities.

DISCLOSURE OF THE INVENTION

It has been shown that the novel hexacyclic compounds represented by the following formula [1],

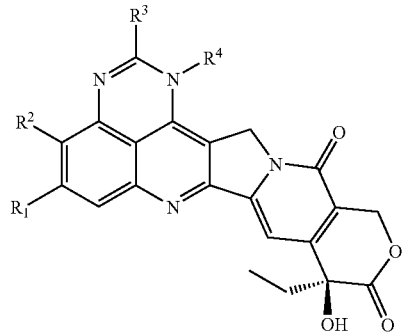

[1]

wherein $R^1$ and $R^2$ are independently hydrogen, halogen, ($C_1$-$C_5$) alkyl or ($C_1$-$C_5$) alkoxy;

$R^3$ is hydrogen;

($C_1$-$C_5$)-allyl optionally substituted with one to three moieties independently selected from the group consisting of ($C_1$-$C_5$)-alkoxy, hydroxy, halogen, amino, ($C_3$-$C_7$)-cycloalkyl, heterocyclic ring or aryl in which the aryl ring is optionally substituted with one to three moieties independently selected from the group consisting of hydroxy, ($C_1$-$C_5$)-alkoxy, amino, mono-($C_1$-$C_5$)alkylamino or di-($C_1$-$C_5$)-alkylamino;

$R^4$ is hydrogen;

($C_1$-$C_{10}$)-alkyl, optionally substituted with one to three moieties independently selected from the group consisting of ($C_1$-$C_5$)-alkoxy, hydroxy, halogen, amino, mono-($C_1$-$C_5$)-alkylamino, di-($C_1$-$C_5$)alkylamino and ($C_3$-$C_7$)-cycloalkyl, a heterocyclic ring and aryl in which the aryl ring is optionally substituted with one to three moieties independently selected from the group consisting of hydroxy, alkoxy, halogen, amino, mono-($C_1$-$C_5$)-alkylamino and di-($C_1$-$C_5$)-alkylamino;

and pharmaceutically acceptable salts thereof, exhibit potent anti-tumor activities during studies using human tumor xenograft models.

The compounds of the formula [1] can be prepared from 9-nitrocamptothecin derivatives as illustrated in the following Scheme 1.

Scheme 1

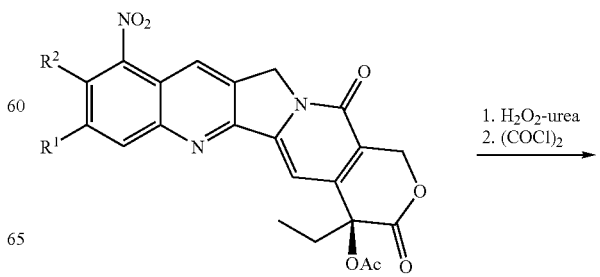

-continued

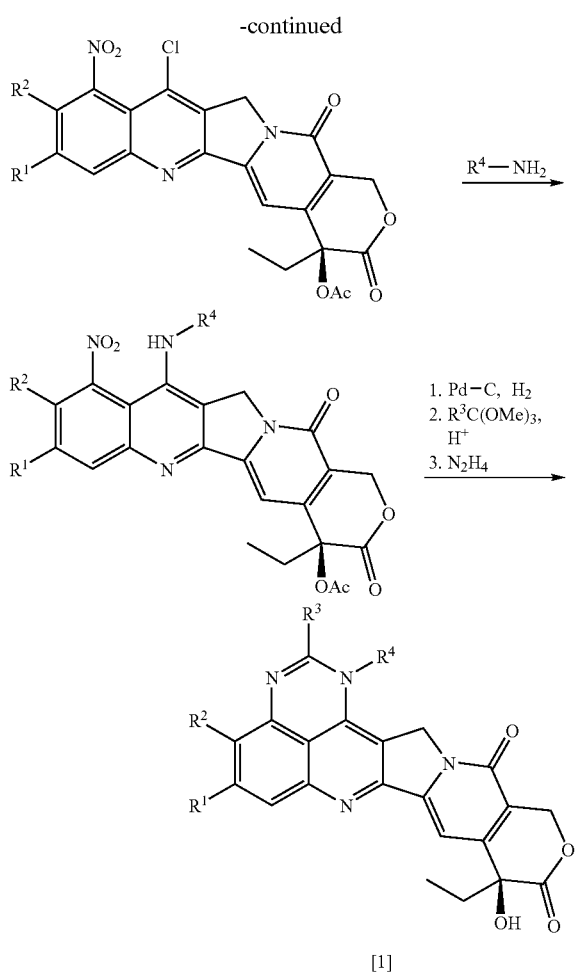

[1]

However, those processes are accompanied with some disadvantages, for example, long linear synthetic steps, low overall yields and many chromatographic purification steps, which set tremendous challenge for the production in industrial scale.

Therefore it is an object of the present invention to provide a novel and more sufficient synthetic process for the preparation of hexacyclic compounds of the formula [1],

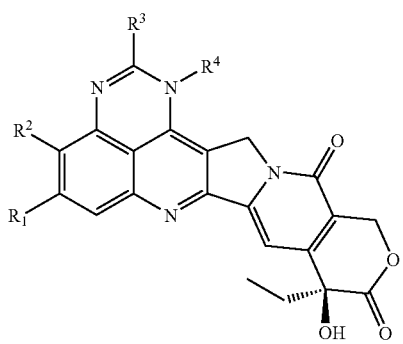

[1]

wherein $R^1$, $R^2$, $R^3$ and $R^4$ are the same as defined above, and pharmaceutically acceptable salts thereof, which comprises condensing a compound of the formula [2] or its salt,

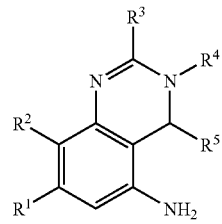

[2]

wherein $R^1$, $R^2$, $R^3$, $R^4$ are the same as defined above and $R^5$ is —OH or —O—($C_1$-$C_5$)-alkyl, with a compound of the formula [3],

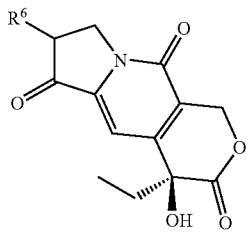

[3]

wherein $R^6$ is chlorine or bromine.

More specifically, it is another object of the present invention to provide a process for the preparation of the compound of the formula [1A],

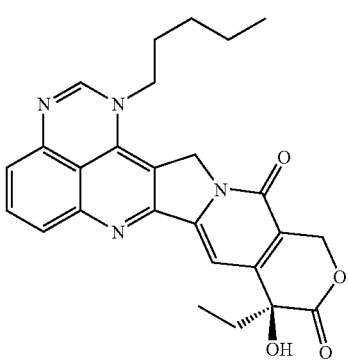

[1A]

which comprises condensing the compound of the formula [2A] or its salt,

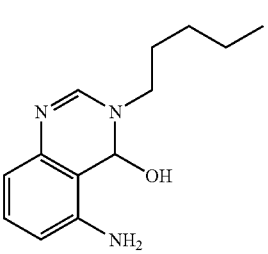

[2A]

with a compound of the formula [3A].

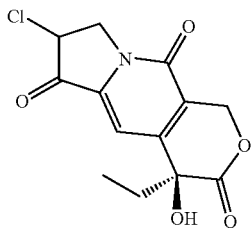
[3A]

It is another object of the present invention to provide a process for the preparation of compounds of the formula [2],

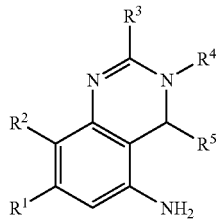
[2]

wherein $R^1$, $R^2$, $R^3$, $R^4$ and $R^5$ are the same as defined above, which comprises a) ozonolysis of compounds of the formula [4] or salts thereof,

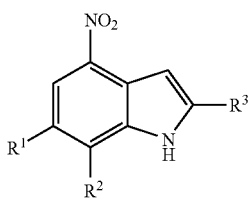
[4]

wherein $R^1$, $R^2$ and $R^3$ are the same as defined above, in order to obtain compounds of the formula [5],

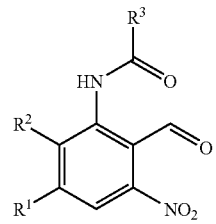
[5]

wherein $R^1$, $R^2$ and $R^3$ are the same as defined above, b) cyclizing the compounds of the formula [5] with amines $R^4$—$NH_2$ ($R^4$ is the same as defined above) in order to obtain compounds of the formula [6],

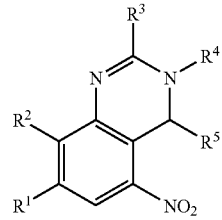
[6]

wherein $R^1$, $R^2$, $R^3$, $R^4$ and $R^5$ are the same as defined above, c) hydrogenating the nitro group of compounds of the formula [6] in order to obtain the compound of the formula [2],

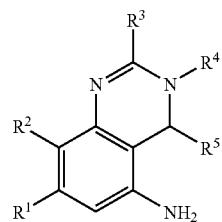
[2]

wherein $R^1$, $R^2$, $R^3$, $R^4$ and $R^5$ are the same as defined above.

Another object of the present invention is to provide a process for the preparation of compounds of the formula [2] which, after ozonolysis of compounds of the formula [4] giving compounds of the formula [5], comprises, d) hydrogenating the nitro group of compounds of the formula [5],

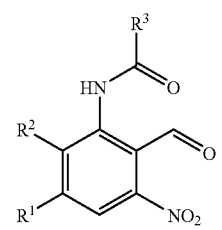
[5]

wherein $R^1$, $R^2$ and $R^3$ are the same as defined above, in order to obtain compounds of the formula [7],

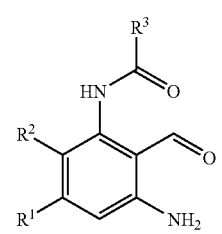
[7]

wherein $R^1$, $R^2$ and $R^3$ are the same as defined above, e) cyclizing compounds of the formula [7] with amines $R^4$—$NH_2$, wherein $R^4$ is the same as defined above, in order to obtain compounds of the formula [2].

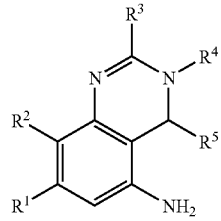
[2]

More specifically, it is another object of the present invention to provide a process for the preparation of the compound of formula [2A] giving the compound of the formula [5A], which comprises a') ozonolysis of a compound of the formula [4A] or its salt,

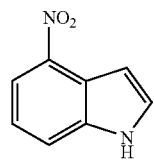
[4A]

in order to obtain the compound of the formula [5A],

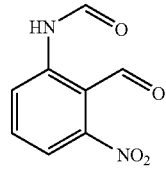
[5A]

b') cyclizing the compound of the formula [5A] with n-pentylamine in order to obtain the compound of the formula [6A],

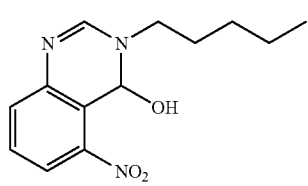
[6A]

c') hydrogenating the nitro group of compound of the formula [6A] in order to obtain the compound of the formula [2A].

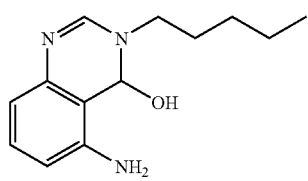
[2A]

Another object of the present invention is to provide a process for the preparation of the compound of the formula [2A] which, after ozonolysis of the compound of the formula [4A] giving the compound of the formula [5A], comprises d') hydrogenating the nitro group of the compound of the formula [5A],

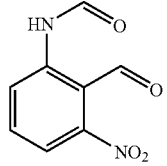
[5A]

in order to obtain the compound of the formula [7A],

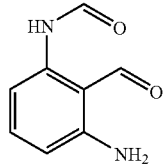
[7A]

e') cyclizing the compound of the formula [7A] with n-pentylamine in order to obtain the compound of the formula [2A].

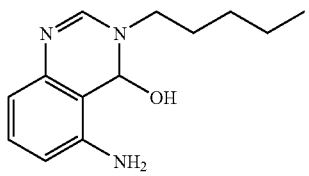
[2A]

It is another object of the present invention to provide a process for the preparation of the compounds of the formula [3], which comprises halogenating the compound of the formula [8]

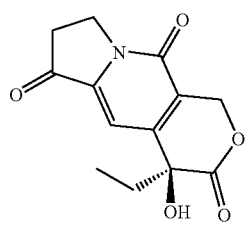
[8]

in order to obtain a compound of formula [3],

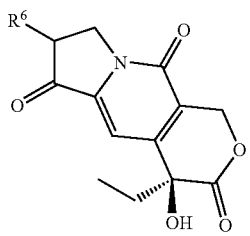
[3]

wherein $R^6$ is chlorine or bromine.

The above mentioned process can be summarized in to the following reaction scheme 2.

Scheme 2

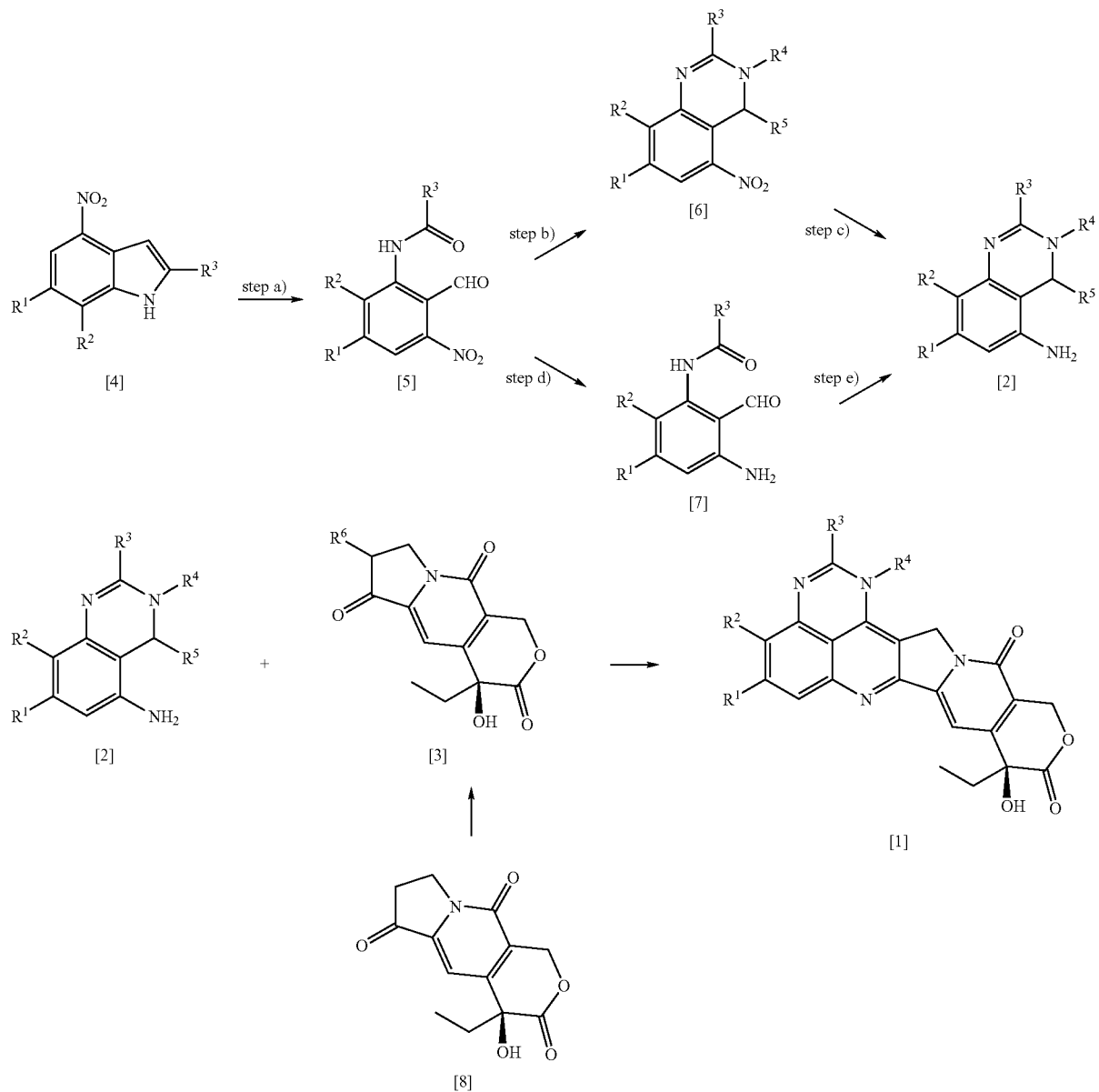

Unless otherwise indicated, the following definitions are set forth to illustrate and to define the meaning and scope of the various terms used to describe the invention herein.

The term "alkyl" refers a straight or branched monovalent saturated aliphatic hydrocarbon group.

"($C_1$-$C_{10}$)-alkyl" means a straight chain or branched hydrocarbon chain having 1 to 10, preferably 1 to 8 carbon atom(s), e.g. methyl, ethyl, propyl, isopropyl, butyl, isobutyl, tert-butyl, sec-butyl, pentyl, 1-methylbutyl, 2-methylbutyl, 3-methylbutyl, 1,1-dimethylpropyl, 2,2-dimethylpropyl, 1-ethylpropyl, hexyl, 1-methylpentyl, 2-methylpentyl, 3-methylpentyl, 4-methylpentyl, 2,2-dimethylbutyl, 2,3-dimethylbutyl, 3,3-dimethylbutyl and the like, more preferably butyl, isobutyl, 3-methylbutyl, or pentyl.

"($C_1$-$C_5$)-alkyl" preferably means methyl, ethyl, propyl, isopropyl, butyl, isobutyl, tert-butyl, sec-butyl, pentyl, 1-methylbutyl, 2-methylbutyl, 3-methylbutyl and the like, more preferably methyl, ethyl, propyl or isopropyl.

The term "alkoxy" refers to the group —O—R', wherein R' is an alkyl group as defined above. "($C_1$-$C_5$)-alkoxy" preferably means methoxy, ethoxy, propoxy, isopropoxy, butoxy, isobutoxy, tert-butoxy, pentoxy, 3-methylbutoxy, 2,2-dimethylpropoxy and the like.

The term "hydroxy" refers to the group HO—.

The term "halogen" refers to fluoro, chloro, bromo and iodo.

The term "amino" refers to the group —$NH_2$ and includes amino groups which are protected by a group known in the art such as a formyl, acetyl, trithyl, tert-butoxycarbonyl, benzyl, benzyloxycarbonyl, and the like. Preferably, it means —$NH_2$.

The term "mono-alkylamino" refers to the group —NH—R', wherein R' is an alkyl group as defined above, and includes amino groups which are protected by a group known in the art such as a formyl, acetyl, trityl, tert-butoxycarbonyl, benzyl, benzyloxycarbonyl, and the like. The term "mono-$(C_1-C_5)$ alkylamino" preferably means N-methylamino, N-ethylamino, N-propylamino, N-isopropylamino, N-butylamino, N-(1-methylpropyl)-amino, N-(2-methylpropyl)amino, N-pentylamino, and the like, more preferably N-ethylamino, N-propylamino, or N-butylamino.

The term "di-alkylamino" refers to the group —NR'R", wherein R' and R" are (independently from each other) an alkyl group as defined above. "di-$(C_1-C_5)$-alkylamino" preferably means N,N-dimethylamino, N,N-diethylamino, N,N-dipropylamino, N,N-diisopropylamino, N,N-dibutylamino, N-methyl-N-ethylamino, N-methyl-N-propylamino and the like, more preferably N,N-dimethylamino, or N,N-diethylamino.

The term "$(C_3-C_7)$-cycloalkyl" means 3 to 7 membered ring, which do not contain any heteroatoms in the ring. "Cycloalkyl" preferably means cyclopropyl, cyclobutyl, cyclopentyl, cyclohexyl, cycloheptyl and the like, more preferably cyclopentyl and cyclohexyl.

The term "heterocyclic ring" refers a 3 to 10 membered heterocyclyl or heteroaryl ring which contains one or more heteroatom(s) selected from N, S and O. Preferably the heterocyclic ring is selected from the group consisting of oxazolyl, thiazolyl, 4,5-dihydro-oxazolyl, 4,5-dihydro-thiazolyl, furyl, pyrrolyl, thienyl, imidazolyl, triazolyl, tetrazolyl, pyridyl, pyrazinyl, pyrimidinyl, triazinyl, oxadiazolyl, thiadiazolyl, pyrrolidinyl, tetrahydrothienyl, tetrahydrofuryl, morpholinyl, piperidyl, piperazinyl, 1-methylpiperazinyl and the like, more preferably imidazolyl, pyridyl, morpholinyl and pyrrolidinyl.

The term "aryl" means an aromatic carbocyclic group, i.e. a 6 or 10 membered aromatic or partially aromatic ring, e.g. phenyl, naphthyl or tetrahydronaphthyl, preferably phenyl or naphthyl, and most preferably phenyl.

In the present invention, the expression "optionally substituted with" means that substitution can occur at one to three positions, preferably at one position, and, unless otherwise indicated, that the substituents are independently selected from the specified options.

The term "pharmaceutically acceptable," such as pharmaceutically acceptable carrier, excipient, prodrug, etc., means pharmacologically acceptable and substantially non-toxic to the subject to which the particular compound is administered.

The term "pharmaceutically acceptable salt" refers to conventional acid-addition salts or base-addition salts which retain the biological effectiveness and properties of the hexacyclic compounds of the formula [1] and are formed from suitable non-toxic organic or inorganic acids or organic or inorganic bases. The acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid and the like. The base-addition salts include those derived from potassium, sodium, ammonium, and quarternary ammonium hydroxide, such as for example tetramethylammonium hydroxide.

In the above definitions, the preferable embodiments of $R^3$ are hydrogen, methyl, ethyl, propyl, isopropyl, butyl, pentyl, hydroxymethyl, methoxymethyl, acetoxymethyl, aminomethyl, (methylamino)methyl, (dimethylamino)methyl, fluoromethyl, chloromethyl, trifluoromethyl, phenyl, pyridin-2-yl, methoxy, ethoxy, methylthio, ethylthio, amino, methylamino, ethylamino, propylamino, butylamino, dimethylamino, diethylamino and the like, and more preferably hydrogen, methyl, ethyl, propyl, hydroxymethyl, aminomethyl, chloromethyl, trifluoromethyl.

The preferable embodiments of $R^4$ are methyl, ethyl, propyl, isopropyl, butyl, isobutyl, pentyl, 3-methylbutyl, 2,2-dimethylpropyl, 1-ethylpropyl, hexyl, 4-methylpentyl, 3,3-dimethylbutyl, heptyl, 2-methoxyethyl, 2-ethoxyethyl, 2-propoxyethyl, 3-methoxypropyl, 4-methoxybutyl, 2-hydroxyethyl, 3-hydroxypropyl, 4-hydroxybutyl, 5-hydroxypentyl, 2-fluoroethyl, 3-fluoropropyl, 4-fluorobutyl, 2-chloroethyl, 3-chloropropyl, 4-chlorobutyl, 2-(dimethylamino) ethyl, 3-(dimethylamino)propyl, 2-(cyclohexyl)ethyl, 2-(4-morpholino)ethyl, 2-(pyyrrolidino)ethyl, 2-(piperidino) ethyl, 2-(4-methylpiperazino)ethyl, 2-(pyridin-2-yl)ethyl, 2-(pyridin-3-yl)ethyl, 2-(imidazol-1-yl)ethyl, benzyl, phenethyl, 2-(1-naphthyl)ethyl, 3-phenylpropyl, 2-(4-fluorophenyl)ethyl, 2-(4-chlorophenyl)ethyl, 2-(4-methoxyphenyl) ethyl, 2-(4-hydroxyphenyl)ethyl, 2-[4-(dimethylamino) phenyl]ethyl, 2-(3,4-methyenedioxyphenyl)ethyl and the like, more preferably methyl, ethyl, propyl, isopropyl, butyl, isobutyl, pentyl, 3-methylbutyl, hexyl, 3,3-dimethylbutyl, heptyl, 2-hydroxyethyl, 3-hydroxypropyl, 2-(dimethylamino)ethyl, 3-(dimethylamino)propyl, 2-(4-morpholino) ethyl, 2-(pyridin-2-yl)ethyl, 2-(pyridin-3-yl)ethyl, benzyl, phenethyl, 3-phenylpropyl, 2-(4-fluorophenyl)ethyl, 2-(4-chlorophenyl)ethyl, 2-(4-methoxyphenyl)ethyl and the like.

In more detail, the present invention refers to a process for the preparation of a compound of the formula [1],

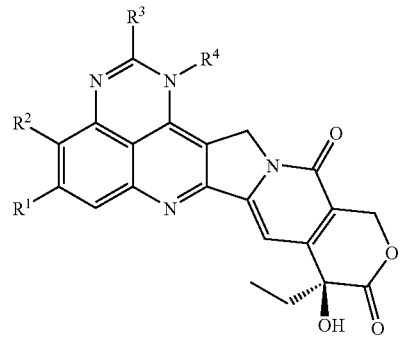

wherein
$R^1$ and $R^2$ are independently hydrogen, halogen, $(C_1-C_5)$-alkyl or $(C_1-C_5)$-alkoxy;
$R^3$ is hydrogen;
$(C_1-C_5)$-alkyl optionally substituted with one to three moieties independently selected from the group consisting of $(C_1-C_5)$-alkoxy, hydroxy, halogen, amino, $(C_3-C_7)$-cycloalkyl, heterocyclic ring or aryl in which the aryl ring is optionally substituted with one to three moieties independently selected from the group consisting of hydroxy, $(C_1-C_5)$-alkoxy, amino, mono-$(C_1-C_5)$-alkylamino or di-$(C_1-C_5)$-alkylamino;
$R^4$ is hydrogen;
$(C_1-C_{10})$-alkyl, optionally substituted with one to three moieties independently selected from the group consisting of $(C_1-C_5)$-alkoxy, hydroxy, halogen, amino, mono-$(C_1-C_5)$-alkylamino, di-$(C_1-C_5)$-alkylamino and $(C_3-C_7)$-cycloalkyl, a heterocyclic ring or aryl in which the aryl ring is optionally substituted with one to three moieties independently selected from the group consisting of hydroxy, alkoxy, halogen, amino, mono-$(C_1-C_5)$-alkylamino and di-$(C_1-C_5)$-alkylamino;

and pharmaceutically acceptable salts thereof,
which comprises condensing a compound of the formula [2] or its salt,

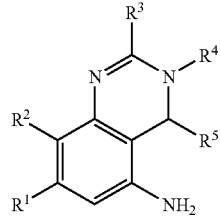

[2]

wherein $R^1$, $R^2$, $R^3$, $R^4$ are the same as defined above and $R^5$ is —OH or O—$(C_1-C_5)$-alkyl,
with a compound of the formula [3] wherein $R^6$ is a chlorine or bromine,

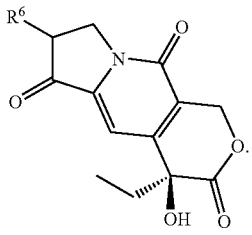

[3]

The condensation reaction of [2] and [3] to compound [1] is preferably carried out in suitable solvent in the presence or absence of an acid catalyst. Preferred solvents are methanol, ethanol, toluene, dichloromethane, chloroform, acetic acid and formic acid as like, most preferably acetic acid and formic acid. Preferred acid catalysts are hydrochloric acid, p-toluenesulfonic acid, and trifluoroacetic acid. The reaction is preferably conducted at the temperature between room temperature to 150° C., more preferably between 50° C. to 100° C.

More preferably, the process of the present invention is for the preparation of compounds of formula [1], wherein
$R^1$ is hydrogen; and
$R^2$ is hydrogen or $(C_1-C_3)$-alkyl;
$R^3$ is hydrogen;
$(C_1-C_5)$-alkyl optionally substituted with one to three moieties independently selected from the group consisting of $(C_1-C_5)$-alkoxy, hydroxy, halogen, amino, $(C_3-C_7)$-cycloalkyl, a heterocyclic ring and aryl; and
$R^4$ is hydrogen;
$(C_1-C_8)$-alkyl which is optionally substituted with one to three moieties independently selected from the group consisting of $(C_1-C_3)$-alkoxy, hydroxy, halogen, amino, mono-$(C_1-C_3)$-alkylamino, di-$(C_1-C_3)$-alkylamino, $(C_3-C_7)$-cycloalkyl, a heterocyclic ring and aryl in which the aryl ring is optionally substituted with one to three moieties independently selected from the group consisting of hydroxy, alkoxy and halogen.

Most preferably, the process of the present invention concerns the preparation of compounds of the formula [1], wherein
$R^1$ and $R^2$ are hydrogen;
$R^3$ is hydrogen, methyl, ethyl, propyl, hydroxymethyl, aminomethyl, (methylamino)methyl, (dimethylamino)methyl, chloromethyl, trifluoromethyl; and
$R^4$ is methyl, ethyl, n-propyl, 1-methylethyl, n-butyl, 1,1-dimethylethyl, 2-methylpropyl, 2,2-dimethylpropyl, n-pentyl, 3-methylbutyl, 2-n-hexyl, 3,3-dimethylbutyl, n-heptyl, n-octyl, benzyl, phenethyl, 2-(dimethylamino)ethyl, 2-(4-morpholino)ethyl, 3-(dimethylamino)propyl, 2-(pyridin-2-yl)ethyl, 2-(pyridin-3-yl)ethyl, 2-(4-methoxyphenyl)ethyl, 2-(4-chlorophenyl)ethyl or 2-(4-fluorophenyl)ethyl, 3-phenylpropyl.

Examples for compounds of the formula [1] prepared by the process are compounds selected from the group consisting of:
a) (9S)-1-butyl-9-ethyl-9-hydroxy-1H,12H-pyrano[3",4":6',7']indolizino-[1',2':6,5]pyrido[4,3,2-de]quinazoline-10,13(9H, 15H)-dione;
b) (9S)-9-ethyl-9-hydroxy-1-[2-(4-morpholino)ethyl]-1H,12H-pyrano[3",4":6',7']-indolizino-[1',2':6,5]pyrido[4,3,2-de]quinazoline-10,13(9H,15H)-dione hydrochloride;
c) (9S)-9-ethyl-9-hydroxy-1-propyl-1H,12H-pyrano[3",4":6',7']indolizino[1',2':6,5]-pyrido-[4,3,2-de]quinazoline-10,13(9H,15H)dione;
d) (9S)-1-benzyl-9-ethyl-9-hydroxy-1H,12H-pyrano[3",4":6'7']indolizino-[1'2':6,5]pyrido[4,3,2-de]quinazoline-10,13(9H,15H)-dione;
e) (9S)-9-ethyl-9-hydroxy-1-phenethyl-1H,12H-pyrano[3",4":6'7']indolizino-[1'2':6,5]pyrido[4,3,2-de]quinazoline-10,13(9H,15H)-dione;
f) (9S)-2,9-diethyl-9-hydroxy-1-phenethyl-1H,12H-pyrano[3",4":6'7']indolizino-[1'2':6,5]pyrido[4,3,2-de]quinazoline-10,13(9H,15H)-dione;
g) (9S)-9-ethyl-9-hydroxy-1-(3-phenylpropyl)-1H,12H-pyrano[3",4":6'7']indolizino-[1'2':6,5]pyrido[4,3,2-de]quinazoline-10,13(9H,15H)-dione;
h) (9S)-9-ethyl-9-hydroxy-1-(3-methylbutyl)-1H,12H-pyrano[3",4":6'7']indolizino-[1'2':6,5]pyrido[4,3,2-de]quinazoline-10,13(9H,15H)-dione;
i) (9S)-2,9-diethyl-9-hydroxy-1-(3-methylbutyl)-1H,12H-pyrano[3",4":6'7']-indolizino-[1'2':6,5]pyrido[4,3,2-de]quinazoline-10,13(9H,15H)-dione;
j) (9S)-2,9-diethyl-9-hydroxy-1-(2-methylpropyl)-1H,12H-pyrano[3",4":6'7']-indolizino[1'2':6,5]pyrido[4,3,2-de]quinazoline-10,13(9H,15H)-dione;
k) (9S)-9-ethyl-1-heptyl-9-hydroxy-1H,12H-pyrano[3",4":6',7']-indolizino[1',2':6,5]pyrido[4,3,2-de]quinazoline-10,13(9H,15H)-dione;
l) (9S)-9-ethyl-9-hydroxy-1-methyl-1H,12H-pyrano[3",4":6',7']-indolizino[1',2':6,5]pyrido[4,3,2-de]quinazoline-10,13(9H,15H)-dione;
m) (9S)-9-ethyl-9-hydroxy-1-(2-methylpropyl)-1H,12H-pyrano[3",4":6',7']indolizino-[1',2':6,5]pyrido[4,3,2-de]quinazoline-10,13(9H,15H)-dione;
n) (9S)-9-ethyl-1-hexyl-9-hydroxy-1H,12H-pyrano[3",4":6',7']indolizino-[1',2':6,5]pyrido[4,3,2-de]quinazoline-10,13(9H,15H)-dione;
o) (9S)-9-ethyl-9-hydroxy-1-pentyl-1H,12H-pyrano[3",4":6',7']indolizino-[1',2':6,5]pyrido[4,3,2-de]quinazoline-10,13(9H,15H)-dione;
p) (9S)-1,9-diethyl-9-hydroxy-1H,12H-pyrano[3",4":6',7']indolizino-[1',2':6,5]pyrido[4,3,2-de]quinazoline-10,13(9H,15H)-dione;
q) (9S)-9-ethyl-9-hydroxy-1-[2-(4-methoxyphenyl)ethyl]-1H,12H-pyrano[3",4":6',7']indolizino-[1',2':6,5]pyrido[4,3,2-de]quinazoline-10,13(9H,15H)-dione;
r) (9S)-1-[2-(4-chlorophenyl)ethyl]-9-ethyl-9-hydroxy-1H,12H-pyrano[3",4":6',7']-indolizino[1',2':6,5]pyrido[4,3,2-de]quinazoline-10,13(9H,15H)-dione;
s) (9S)-9-ethyl-1-[2-(4-fluorophenyl)ethyl]-9-hydroxy-1H,12H-pyrano[3",4":6',7']-indolizino[1',2':6,5]pyrido[4,3,2-de]quinazoline-10,13(9H,15H)-dione;

t) (9S)-9-ethyl-1-[2-(4-fluorophenyl)ethyl]-9-hydroxy-2-methyl-1H,12H-pyrano[3",4":6',7']indolizino[1',2':6,5]pyrido[4,3,2-de]quinazoline-10,13(9H,15H)-dione;

u) (9S)-9-ethyl-9-hydroxy-1-(1-methylethyl)-1H,12H-pyrano[3",4":6',7']-indolizino[1',2':6,5]pyrido[4,3,2-de]quinazoline-10,13(9H,15H)-dione;

v) (9S)-1-(3,3dimethylbutyl)-9-ethyl-9-hydroxy-1H,12H-pyrano[3",4":6',7']-indolizino[1',2':6,5]pyrido[4,3,2-de]quinazoline-10,13(9H,15H)-dione;

w) (9S)-2,9-diethyl-9-hydroxy-1-(3-methylbutyl)-1H,12H-pyrano[3",4":6',7']-indolizino[1',2':6,5]pyrido[4,3,2-de]quinazoline-10,13(9H,15H)-dione;

x) (9S)-9-ethyl-9-hydroxy-1-(2-hydroxyethyl)-1H,12H-pyrano[3",4":6',7']-indolizino[1',2':6,5]pyrido[4,3,2-de]quinazoline-10,13(9H,15H)-dione;

y) (9S)-9-ethyl-9-hydroxy-1-(2-hydroxyethyl)-2-methyl-1H,12H-pyrano[3",4":6',7']-indolizino[1',2':6,5]pyrido[4,3,2-de]quinazoline-10,13(9H,15H)-dione;

z) (9S)-9-ethyl-9-hydroxy-2-methyl-1-pentyl-1H,12H-pyrano[3",4":6',7']-indolizino[1',2':6,5]pyrido[4,3,2-de]quinazoline-10,13(9H,15H)-dione;

aa) (9S)-2,9-diethyl-9-hydroxy-1-pentyl-1H,12H-pyrano[3",4":6',7']-indolizino[1',2':6,5]pyrido[4,3,2-de]quinazoline-10,13(9H,15H)-dione;

bb) (9S)-9-ethyl-9-hydroxy-1-pentyl-2-propyl-1H,12H-pyrano[3",4":6',7']-indolizino[1',2':6,5]pyrido[4,3,2-de]quinazoline-10,13(9H,15H)-dione;

cc) (9S)-9-ethyl-9-hydroxy-2-hydroxymethyl-1-pentyl-1H,12H-pyrano[3",4":6'7']-indolizino[1'2':6,5]pyrido[4,3,2-de]quinazoline-10,13(9H,15H)-dione;

dd) (9S)-9-ethyl-9-hydroxy-2-hydroxymethyl-1-(2-methylpropyl)-1H,12H-pyrano-[3",4":6'7']indolizino[1'2':6,5]pyrido[4,3,2-de]quinazoline-10,13(9H,15H)-dione;

ee) (9S)-9-ethyl-9-hydroxy-2-hydroxymethyl-1-(3-methylbutyl)-1H,12H-pyrano[3",4":6'7']indolizino[1'2':6,5]pyrido[4,3,2-de]quinazoline-10,13(9H,15H)-dione;

ff) (9S)-2-chloromethyl-9-ethyl-9-hydroxy-1-(3-methylbutyl)-1H,12H-pyrano-[3",4":6'7']indolizino[1'2':6,5]pyrido[4,3,2-de]quinazoline-10,13(9H,15H)-dione;

gg) (9S)-2-aminomethyl-9-ethyl-9-hydroxy-1-pentyl-1H,12H-pyrano[3",4":6'7']-indolizino[1'2':6,5]pyrido[4,3,2-de]quinazoline-10,13(9H,15H)-dione; and hh) (9S)-9-Ethyl-9-hydroxy-1-pentyl-2-trifluoromethyl-1H,12H-pyrano[3",4":6',7']indolizino[1',2':6,5]pyrido[4,3,2-de]quinazoline-10,13(9H,15H)-dione.

An especially preferred process of the present invention is that for the preparation of compound of formula [1A], which comprises condensing the compound of the formula [2A] or its salt,

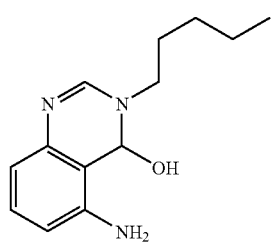

[2A]

with the compound of the formula [3A],

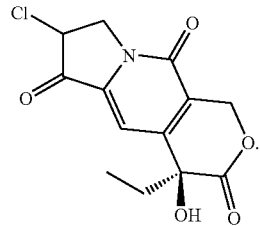

[3A]

Another embodiment of the present invention concerns the process for the preparation of compounds of the formula [2], which comprises a) ozonolysis of the compound of the formula [4] or its salt,

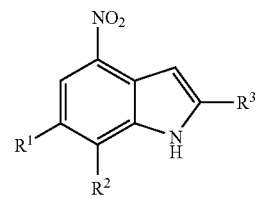

[4]

wherein $R^1$, $R^2$ and $R^3$ are the same as defined above, in order to obtain compound of the formula [5],

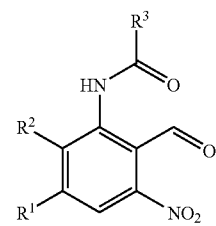

[5]

wherein $R^1$, $R^2$ and $R^3$ are the same as defined above, b) cyclizing the compound of formula [5] with an amine $R^4$—$NH_2$ to obtain a compound of the formula [6],

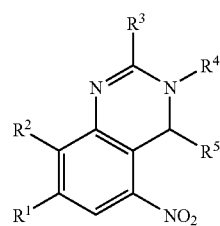

[6]

wherein $R^1$, $R^2$, $R^3$, $R^4$ and $R^5$ are the same as defined above, c) hydrogenating the nitro group of compound of the formula [6] in order to obtain a compound of the formula [2],

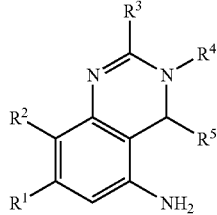
[2]

wherein $R^1$, $R^2$, $R^3$, $R^4$ and $R^5$ are the same as defined above.

Alternatively, the present invention is to provide a process for the preparation of a compound of the formula [2] which, after ozonolysis of a compound of the formula [4] giving a compound of the formula [5], comprises d) hydrogenating the nitro group of compound of the formula [5],

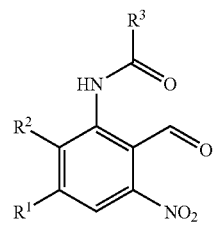
[5]

wherein $R^1$, $R^2$ and $R^3$ are the same as defined above, in order to obtain a compound of the formula [7],

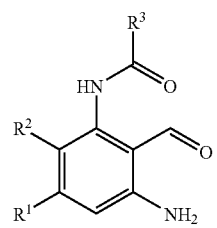
[7]

wherein $R^1$, $R^2$ and $R^3$ are the same as defined above, e) cyclizing the compound of the formula [7] with an amine $R^4$—$NH_2$ in order to obtain a compound of the formula [2],

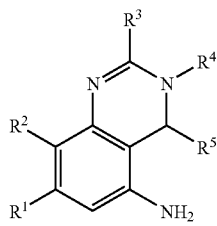
[2]

wherein $R^1$, $R^2$, $R^3$, $R^4$ and $R^5$ are the same as defined above.

The ozonolysis in the above step a) is preferably carried out in a suitable solvent. Suitable solvents are dichloromethane, chloroform, tetrahydrofuran, N,N-dimethylformamide, acetic acid, methanol and water as like and a mixture of solvents indicated above, more preferably dichloromethane, dichloromethane-methanol mixture and dichiloromethane-N,N-dimethylforamide mixture. Typically, the ozonolysis is conducted at the temperature between −78° C. to room temperature for 1 to 10 hours. After completion of the reaction, the reaction mixture may be treated with a suitable reducing reagent. Preferable reducing reagents are dialkyl sulfide such as dimethyl sulfide and diethyl sulfide and trialkyl- or triarylphosphines such as tributylphosphine and triphenyl phosphine, most preferably dimethyl sulfide.

The cyclization in the above step b) or step e) with an amine $R^4$—$NH_2$ is preferably carried out in a suitable organic solvent such as methanol, ethanol, tetrahydrofuran, 1,4-dioxane, chloroform, N,N-dimethyl formamide as like, more preferably methanol and ethanol. The reaction was conducted at the temperature from room temperature to 120° C. for a period of 15 minutes to several days.

The hydrogenation in the above step c) or step d) is preferably carried out with a reducing reagent in a suitable solvent in the presence of a suitable catalyst. Suitable reducing reagents are molecular hydrogen, or hydrogen source such as cyclohexadiene, formic acid, ammonium formate as like. Suitable solvents are e.g., methanol, ethanol, ethyl acetate, N,N-dimethyl formamide, 1,4 dioxane, and water with or without inorganic or organic acid such as 1 to 10 N aqueous hydrochloric acid, sulfonic acid, phosphonic acid, nitric acid, acetic acid, frifluoroacetic acid. Suitable catalysts are transition metals such as palladium, platinum, nickel, and typically are 5 to 20% palladium on charcoal and 5 to 10% palladium hydroxide on charcoal. Typically the reaction is conducted at the temperature 0 to 100° C., at the pressure 1 to 100 atmosphere for a time of 15 minutes to several days. The reaction of the steps c) and e) is also achieved with elemental metal or low-valent metal salt such as Zn, Fe, and $SnCl_2$ in a suitable solvent such as aqueous hydrochloric aid and methanolic hydrochloric acid at the temperature 0 to 100° C. for a period of 15 minutes to several days.

More preferably, the present invention relates to a process for the preparation of a compound of the formula [2A],

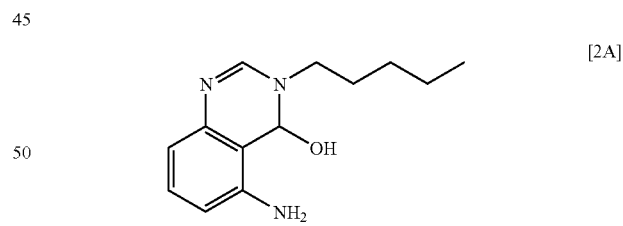
[2A]

which comprises a') ozonolysis of a compound of the formula [4A] or its salt,

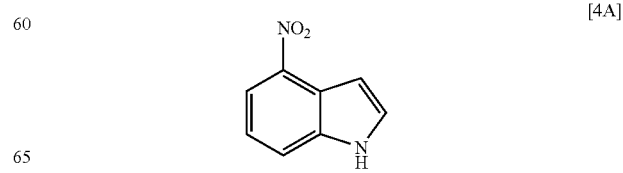
[4A]

in order to obtain compound of the formula [5A],

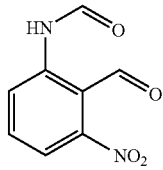
[5A]

b') cyclizing the compound of the formula [5A] with n-pentylamine in order to obtain compound of the formula [6A],

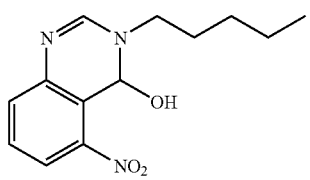
[6A]

and c') hydrogenating the nitro group of compound of the formula [6A] in order to obtain the compound of the formula [2A]

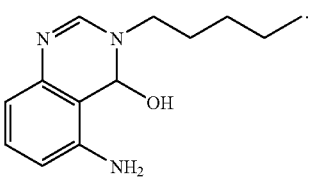
[2A]

Alternatively, the compound of the formula [2A] can be prepared from a compound of the formula [5A] after ozonolysis of step a') according to claim 7, which comprises, d') hydrogenating the nitro group of compound of the formula [5A],

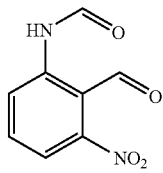
[5A]

in order to obtain the compound of the formula [7A],

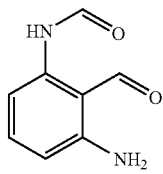
[7A]

and e') cyclizing compound of the formula [7A] with n-pentylamine in order to obtain the compound of the formula [2A].

The present invention further relates to compounds of the formula [2],

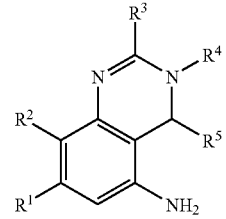
[2]

wherein, $R^1$ and $R^2$ are independently hydrogen, halogen, $(C_1-C_5)$-alkyl or $(C_1-C_5)$-alkoxy;

$R^3$ is hydrogen;

$(C_1-C_5)$-alkyl optionally substituted with one to three moieties independently selected from the group consisting of $(C_1-C_5)$-alkoxy, hydroxy, halogen, amino, $(C_3-C_7)$-cycloalkyl, heterocyclic ring or aryl in which the aryl ring is optionally substituted with one to three moieties independently selected from the group consisting of hydroxy, $(C_1-C_5)$-alkoxy, amino, mono-$(C_1-C_5)$-alkylamino or di-$(C_1-C_5)$-alkylamino;

$R^4$ is hydrogen;

$(C_1-C_{10})$-alkyl, optionally substituted with one to three moieties independently selected from the group consisting of $(C_1-C_5)$-alkoxy, hydroxy, halogen, amino, mono-$(C_1-C_5)$-alkylamino, di-$(C_1-C_5)$-alkylamino and $(C_3-C_7)$-cycloalkyl, a heterocyclic ring or aryl in which the aryl ring is optionally substituted with one to three moieties independently selected from the group consisting of hydroxy, alkoxy, halogen, amino, mono-$(C_1-C_5)$-alkylamino and di-$(C_1-C_5)$-alkylamino; and $R^5$ is —OH or —O—$(C_1-C_5)$-alkyl.

Most preferably, said compound is 5-amino-4-hydroxy-3-pentyl-3,4-dihydroquinazoline [2a].

Further the present invention concerns also a process for the preparation of compounds of the formula [3], which comprises halogenating a compound of the formula [8],

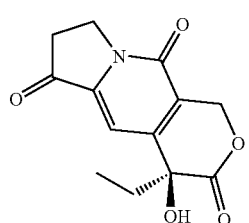
[8]

in order to obtain compound of the formula [3],

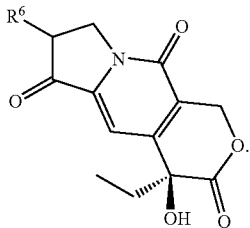

[3]

wherein $R^6$ is chlorine or bromine.

The halogenation for the above step is preferably performed with a halogenating reagent in a suitable solvent. Suitable hologenating reagents are sulfuryl chloride, N-chlorosuccimide, t-butyl hypochloride, bromine, N-bromosuccimide as like. Suitable solvents are preferably dichloromethane, chloroform, acetic acid, formic acid, and tetrahydrofuran as like. Typically the reaction is conducted at the temperature −30 to 50° C., more preferably at the temperature 0° C. to room temperature.

The invention also relates to the compounds of the formula [3],

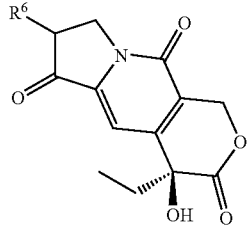

[3]

wherein $R^6$ is chlorine or bromine.

Most preferably, the compound of formula [3] is (4S)-6-chloro-4-ethyl-7,8-dihydro-4-hydroxy-1H-pyrano[3,4-f]-indolizine-3,6,10(4H)-trione [3a].

Another embodiment of the present invention concerns a process for the preparation of a compound of the formula [1] which comprises condensing a compound of the formula [2] prepared by the process as defined above with a compound of the formula [3] prepared by the process as defined above.

The hexacyclic compounds of the present invention are effective at inhibiting or preventing the growth of tumors in premalignant and malignant cells and are useful for the treatment of carcinomas forming solid tumors, especially of colorectal cancer, lung cancer, breast cancer, stomach cancer, cervical cancer and bladder cancer. The hexacyclic compounds of the present invention can be used to treat such tumors, to retard the development of such tumors, and to prevent the increase in number of tumors.

The anti-cancer therapeutic activity of the hexacyclic compounds of this invention may be demonstrated by various standard in vitro assays. Such assays described below and in the examples are known to indicate anticancer activity and are assays for cancer therapeutics. The hexacyclic compounds of the present invention have the structure depicted in the formula [1], and anticancer activity as determined by any standard assay, especially assays for apoptosis. The hexacyclic compounds of this invention are particularly effective to induce apoptosis in carcinoma cells, causing the death of the cell. Thus the hexacyclic compounds of this invention are the desired activities if the compounds cause carcinoma cells to die when the cells are exposed to the hexacyclic compounds of this invention. Carcinoma cells for assays (for example breast, lung, colorectal, etc.) are readily obtained from cells depositories such as the American Type Culture Collection (ATCC) or may be isolated by skilled persons from cancer patients. The type of cancer against which the hexacyclic compounds of this invention are most active is determined by the type of cells used in the assays.

Carcinoma cells, grown in culture, may be incubated with a specific compound and changes in cells viability may be determined for example, by dyes which selectively stain dead cells or by optical density (O.D.) measurement. If more than 10% of cells have died, the compound is active in inducing apoptosis. The compounds may not directly kill the cells (cellular toxicity) but may modulate certain intra- or extracellular events which result in apoptosis. The anticancer activity of the compounds of this invention may also be determined by assays that access the effects of compounds on cells growth and differentiation. Cell growth inhibition may be determined by adding the compound in question to carcinoma cells in culture with dyes or radioactive precursors, and determining by microscopic cell counting, scintillation counting, or O.D. measurement whether the number of cells has increased over the incubation period. If the number of cells has not increased, growth has been inhibited and the compound is regarded as having therapeutic activity. Similarly, the proportion of cells which have become differentiated after addition of a test compound may be determined by known methods (i.e. measuring oxidative burst in HL-60 cells, an indicator of differentiation, by NBT(nitroblue tetrazolium). If 10% or more cells have differentiated, then the compound is regarded as having therapeutic activity.

The Antiproliferative activity assay was carried out as follows. A single suspension of tumor cells was inoculated to the serially diluted 96-well microtestplate. Then the testplate was incubated in the 5% $CO_2$ ambience at 37° C. for 4 days ($2-3\times10^3$ cells/well). The degree of cell growth in a monolayer was measured by using WST-8 (Dojindo, Japan). $IC_{50}$ values of drugs against tumor cells were calculated as the concentration of drug yielding 50% OD of the control growth. The $IC_{50}$ value measures the drug concentration for 50% of the growth of tumor cells in vitro as compared to the control. The results are shown in the following Table 1.

Anti-tumor activities of hexacyclic compounds of formula [1] against in vitro growth of human tumor cell lines, HCT116 and DLD-1 of colorectal cancer (CRC) and QG56 and NCI-H460 of non small cell lung cancer (NSCLC) are shown in Table 1. These cell lines are commercially available via the American Type Culture Collection (ATTC).

In Table 1,

Compound A denotes (9S)-9-ethyl-9-hydroxy-1-pentyl-1H, 12H-pyrano[3",4":6',7']-indolizino[1',2':6,5]pyrido[4,3,2-de]quinazoline-10,13(9H,15H)-dione.

Compound B denotes (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)dione.

Compound C denotes (9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H, 15H)dione.

SN-38 denotes 7-ethyl-10-hydroxycamptothecin.

TABLE 1

| | Anti-proliferative activity assay (IC$_{50}$ in nM) | | | |
|---|---|---|---|---|
| Compound | HCT116 (CRC) | DLD-1 (CRC) | QG56 (NSCLC) | NCI-H460 (NSCLC) |
| Compound A | 6.1 | 23 | 7.7 | 7.0 |
| Compound B | 4.5 | 15 | 15 | 7.9 |
| Compound C | 3.1 | 12 | 7.4 | 4.8 |
| SN-38 (Reference) | 6.9 | 53 | 27 | 21 |

For clinical use, the hexacyclic compounds of the formula [1], their prodrugs, or salt forms thereof and the like can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, rectal or topical administration.

In more detail, as mentioned earlier, pharmaceutical compositions containing a compound of the formula [1] or its prodrug are also an aspect of the present invention, as is a process for the manufacture of such medicaments, whose process comprises bringing one or more compounds of the formula [1] and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragées or hard gelatine capsules, the hexacyclic compounds of the present invention may be admixed with pharmaceutically inert, inorganic or organic excipients (pharmaceutically acceptable carriers). Examples of suitable excipients for tablets, dragées or hard gelatine capsules include lactose, maize starch or derivatives thereof, talc or stearic acid or salts thereof. Suitable excipients for use with soft gelatine capsules include, for example, vegetable oils, waxes, fats, semi-solid or liquid polyols etc.; according to the nature of the active ingredients it may however be the case that no excipient is needed at all for soft gelatine capsules. For the preparation of solutions and syrups, excipients which may be used include for example water, polyols, saccharose, invert sugar and glucose. For injectable solutions, excipients which may be used include for example water, alcohols, polyols, glycerine, and vegetable oils. For suppositories, and local or percutaneous application, excipients which may be used include for example natural or hardened oils, waxes, fats and semi-solid or liquid polyols.

The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents.

In summary, a pharmaceutical formulation for oral administration may be granule, tablet, sugar coated tablet, capsule, pill, suspension or emulsion, which for parenteral injection, for example, intravenously, intramuscularly or subcutaneously, may be used in the form of a sterile aqueous solution which may contain other substances, for example, salts or glucose to make the solution isotonic. The anti-tumor agent can also be administered in the form of a suppository or pessary, or they may be applied topically in the form of a lotion, solution, cream, ointment or dusting powder.

The daily dosage level of the hexacyclic compounds of the present invention is from 5 to 2,000 mg/m$^2$ when administered by either the oral or parenteral route. Thus tablets or capsules can contain from 5 mg to 1,000 mg of active compound for single administration or two or more at a time as appropriate. In any event the actual dosage can be weight and response of the particular patient.

The following examples illustrate the preferred methods for the preparation of the hexacyclic compounds of the present invention, which are not intended to limit the scope of the invention thereto.

EXAMPLES

1. Preparation of N-(2-formyl-3-nitrophenyl)formamide [5a]

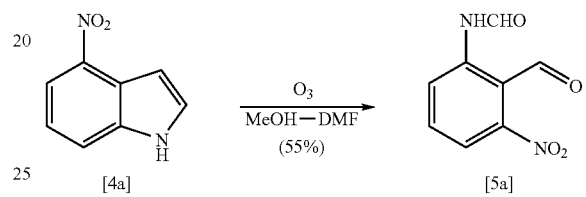

A stirred solution of 4-nitro-1H-indole (4a, 93.8 g, 0.56 mol) in DMF-MeOH (1:2, 2.7 L) cooled in a dry ice-acetone bath was bubbled with ozone (generated from oxygen gas, 22 g/m$^3$, flow rate 500 L/hr, ozone generator: Tokyo Keiso, 11 g/hr) for 3.5 h. The mixture was kept cool in the dry ice-acetone bath for 1 h without stirring. The precipitate generated was filtered and washed with H$_2$O to give N-(2-formyl-3-nitrophenyl)-formamide (5a, 62.0 g, 55%), $^1$H NMR (270 MHz) δ (DMSO-d$_6$) 7.82 (t, J=7.9 Hz, 1H), 7.91 (d, J=7.9 Hz, 1H), 8.15 (m, 1H), 8.37 (br, 1H), 10.07 (s, 1H), 10.71 (br, 1H); MS (EI) m/z 194 (M$^+$).

2. Preparation of 4-hydroxy-5-nitro-3-pentyl-3,4-dihydroquinazoline [6a]

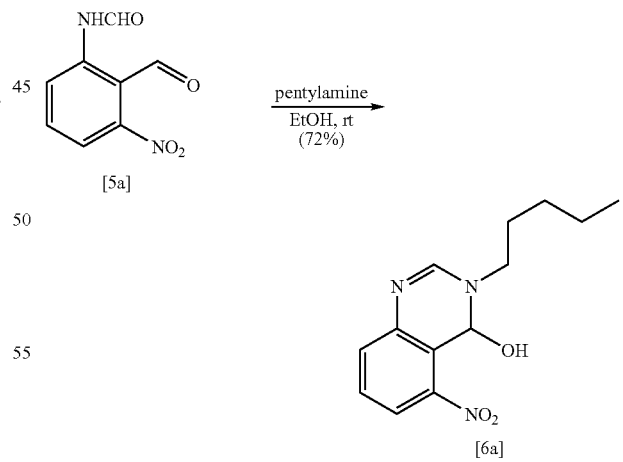

N-(2-Formyl-3-nitrophenyl)formamide (5a, 20.0 g, 103 mmol) and n-pentylamine (23.9 ml, 206 mmol) were dissolved in EtOH (240 ml) and the mixture stirred at room temperature for 3 h. After the mixture was concentrated under reduced pressure, EtOAc (100 ml) was added to the residue, and the generating yellow crystal was collected by filtration. The crystal was washed with EtOAc and dried under vacuum to obtain 4-hydroxy-5-nitro-3-pentyl-3,4-dihydroquinazoline (6a, 19.6 g, 72%); $^1$H NMR (270 MHz) δ (CDCl$_3$) 0.91 (t, J=6.7 Hz, 3H), 1.26-1.38 (m, 4H), 1.67-1.78 (m, 2H), 3.21 (dt, J=13.9 and 7.9 Hz, 1H), 3.77 (ddd, J=6.3, 7.6 and 13.9 Hz, 1H), 6.57 (s, 1H), 6.90 (s, 1H), 7.30-7.41 (m, 2H), 7.80 (dd, J=1.7 and 7.6 hz, 1H); MS (ES) m/z 264 (M$^+$+1).

3. Preparation of N-(3-amino-2-formylphenyl)formamide [7a]

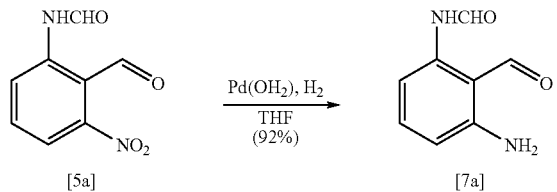

N-(2-Formyl-3-nitrophenyl)formamide (5a, 51.6 g, 0.27 mol) was dissolved in THF (1 L) and 20 wt % Pd(OH)$_2$ on activated charcoal (4.96 g) was added. Hydrogenation was carried out at 37° C. in an oil bath under H$_2$ atmosphere. After being stirred for 4 h, an additional 20 wt % Pd(OH)$_2$ on activated charcoal (2.01 g) was added and the hydrogenation was continued further at 37° C. in an oil bath. After 22 h, the mixture was filtered and the Pd catalyst separated was washed with THF. The combined filtrate and washing were concentrated under reduced pressure. The generated crude solid was suspended in H$_2$O (500 mL) and then the orange powder was collected by filtration, washed with H$_2$O, and dried under vacuum to obtain N-(3-amino-2-formylphenyl)-formamide (7a, 40.2 g, 92%); $^1$H NMR (270 MHz) δ (CD$_3$OD): rotamer A (major)* 6.53 (d, J=7.9 Hz, 1H), 6.66 (d, J=7.9 Hz, 1H), 7.17 (t, J=7.9 Hz, 1H), 8.23 (s, 1H), 9.97 (s, 1H); rotamer B (minor)* 6.33 (d, J=7.9 Hz, 1H), 6.54 (d, J=7.9 Hz, 1H), 7.17 (t, J=7.9 Hz, 1H), 8.40 (s, 1H), 10.05 (s, 1H). The ratio of two rotamers A and B is approximately 2:1.

$^1$H NMR (400 MHz) δ (DMSO-d$_6$, 120° C.); 6.60 (d, J=8.0 Hz, 1H), 6.70 (m, 1H), 6.97 (br, 2H), 7.24 (t, J=8.0 Hz, 1H), 8.41 (s, 1H), 10.10 (s, 2f); MS (EI) m/z 164 (M$^+$).

4. Preparation of 5-amino-4-hydroxy-3-pentyl-3,4-dihydroquinazoline [2a] from [6a]

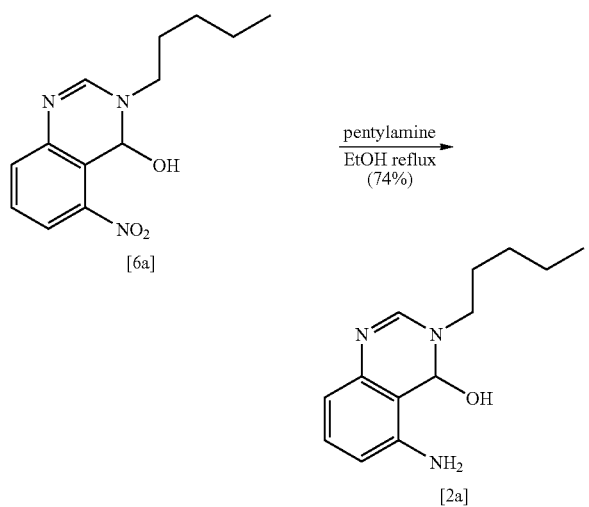

4-hydroxy-5-nitro-3-pentyl-3,4-dihydroquinazoline (6a, 10.0 g, 38.0 mmol) was dissolved in EtOAc-MeOH mixed solvent (2:1, 150 ml) and 3% Pt—C (1.0 g) was added. Hydrogenation was carried out at room temperature under H$_2$ atmosphere using a balloon. After 2 h, the reaction was stopped and the mixture was filtered. The filtrated was concentrated under reduced pressure and the obtaining residual oil was purified by a short silica gel (100 g) column chromatography (eluent: EtOAc/MeOH=20/1) to give 5-amino-4-hydroxy-3-pentyl-3,4-dihydroquinazoline (2a, 6.56 g, 74%); $^1$H NMR (270 MHz) δ (CD$_3$OD) 0.88 (t, J=6.9 Hz, 3H), 1.23-1.41 (m, 4H), 1.63-1.74 (m, 2H), 3.26-3.35 (m, 1H), 3.51-3.62 (m, 1H), 6.15 (s, 1H), 6.47-6.51 (m, 1H), 6.55 (dd, J=1.0 and 7.9 Hz, 1H), 7.06 (t, J=7.9 Hz, 1H), 7.43 (s, 1H); MS (ES) m/z 234 (M$^+$).

5. Preparation of 5-amino-4-hydroxy-3-pentyl-3,4-dihydroquinazoline [2a] from [7a]

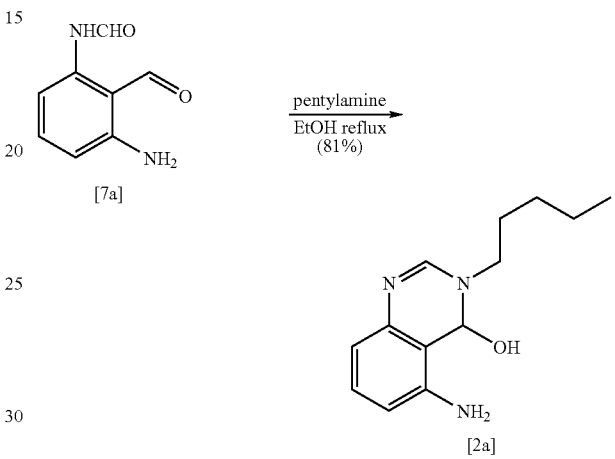

N-(3-amino-2-formylphenyl)formamide (7a, 40.1 g, 0.24 mol) and n-pentylamine (34.0 ml, 0.29 mol) were dissolved in EtOH (830 mL) and the mixture was heated to reflux for 6 h in an oil bath. After being cooled to room temperature, the mixture was concentrated under reduced pressure. The obtained residual oil was purified by silica gel column chromatography (eluent: EtOAc only and then EtOAc/MeOH=20/1) to give 5-amino-4-hydroxy-3-pentyl-3,4-dihydroquinazoline (2a, 48.8 g, 81%).

6. Preparation of (4S)-6-chloro-4-ethyl-7,8-dihydro-4-hydroxy-1H-pyrano[3,4-f]-indolizine-3,6,10(4H)-trione [3a]

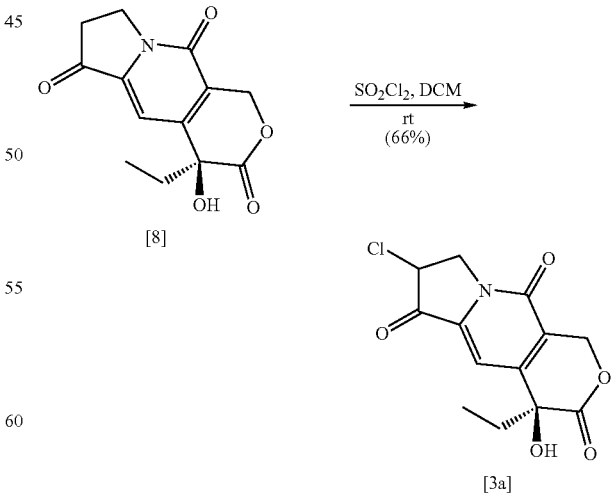

To a solution of (S)-4-ethyl-7,8-dihydro-4-hydroxy-1H-pyrano[3,4-f]indolizine-3,6,10(4H)-trione (8, 40.7 g, 0.155 mol) in dichloromethane (750 ml) was added sulfuryl chloride (15.0 ml, 187 mmol) dropwise over 15 min at room temperature. The mixture was stirred at room temperature for 14 hr, and the precipitate generated was collected by filtration. The solid was suspended in dichloromethane (300 ml) and the solid was collected by filtration followed by drying under vacuum to give the first crop of pure (4S)-6-chloroethyl-7,8-dihydro-4-hydroxy-1H-pyrano[3,4-f]indolizine-3,6,10(4H)-trione (3a, 21.4 g, 46%) as an off-white solid. The filtrates were combined and concentrated under reduced pressure to give a residual solid, which was suspended in dichloromethane (200 ml). The solid was collected by filtration and then washed in dichloromethane (200 ml). The solid was collected by filtration and dried under vacuum to obtain the product (3a, 9.3 g, 20%) as an off-white solid; $^1$H-NMR (270 Mz, CDCl$_3$) δ 0.90-1.04 (m, 3H), 1.72-1.91 (m, 2H), 3.69 (s, 1H), 4.31-4.42 (m, 1H), 4.66-4.83 (m, 2 H), 5.24 (d, J=17.3 Hz, 1H), 5.67 (d, J=17.3 Hz, 1H), 7.35 (m, 1H).

NMR spectrum in DMSO-d$_6$ showed the existence of tautomeric mixture of keto/enol forms (1:2). $^1$H NMR (270 MHz, DMSO-d$_6$) δ Enol form: 0.68-0.89 (m, 3H), 1.65-1.90 (m, 2H), 4.59 (s, 2H), 5.31 (s, 2H), 6.36 (br, 1H), 6.75 (s, 1H), 10.99 (s, 1H); Keto form: 0.68-0.89 (m, 3H), 1.65-1.90 (m, 2H), 4.06-4.18 (m, 1H), 4.63-4.73 (m, 1H), 5.12-5.19 (m, 1H), 5.30-5.50 (m, 2H), 6.56 (br, 1 M), 7.00 (s, 1H).

7. Preparation of (9S)-9-ethyl-9-hydroxy-1-pentyl-1H,12H-pyrano[3",4":6',7']-indolizino[1',2':6,5]pyrido[4,3,2-de]quinazoline-10,13(9H,15H)-dione [1a]

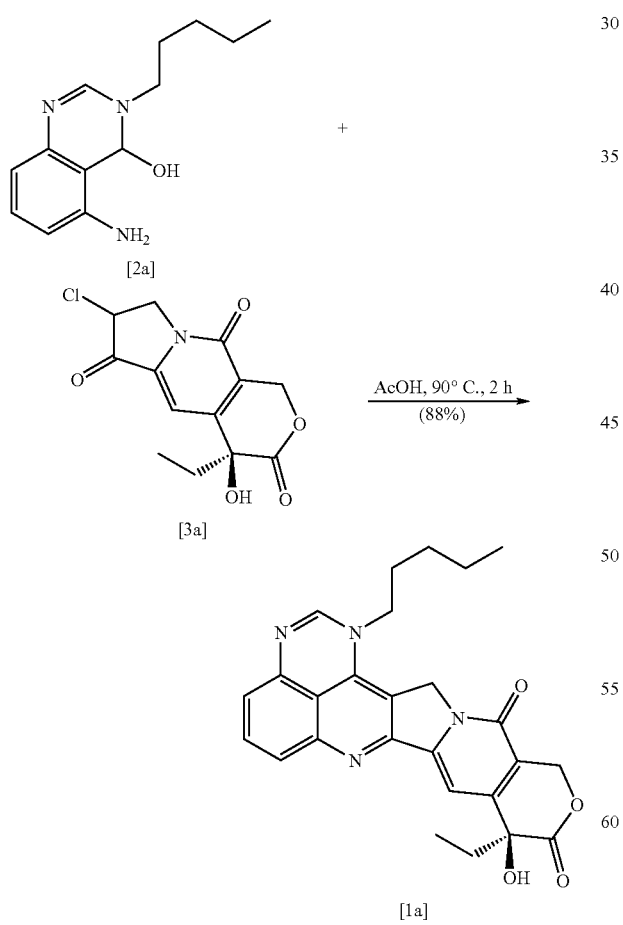

(4S)-6-Chloro-4-ethyl-7,8-dihydro-4-hydroxy-1H-pyrano[3,4-f]indolizine-3,6,10(4H)-trione (3a, 17.69 g, 59.4 mmol) and 5-amino-4-hydroxy-3-pentyl-3,4-dihydroquinazoline (2a, 13.86 g, 56.0 mmol) were combined in acetic acid (300 mL), and the mixture was heated at 90° C. for 2.5 h in an oil bath. After cooling to room temperature, the mixture was concentrated under reduced pressure. Water (350 mL) was added to the residue and the generating solid was collected by filtration, washed with ethanol-water (1:3, 120 ml) and dried under reduced pressure to give (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione (1a, 22.65 g, 88%) as a brownish solid.

$^1$H NMR (270 MHz, DMSO-d$_6$)) δ 0.85-0.92 (m, 6H), 1.35-1.38 (m, 4H), 1.75-1.93 (m, 4H), 3.89-3.94 (m, 2H), 5.29 (s, 2H), 5.40 (s, 2H), 6.46 (s, 1H), 6.99 (dd, J=1.0, 7.4 Hz, 1H), 7.18 (s, 1H), 7.47 (dd, J=1.0, 8.6 Hz, 1H), 7.62 (dd, J=7.4, 8.6 Hz, 1H), 7.86 (s, 1H); MS (ES) m/z 459 (M$^+$+1).

The invention claimed is:

1. A process for the preparation of a compound of the formula [1],

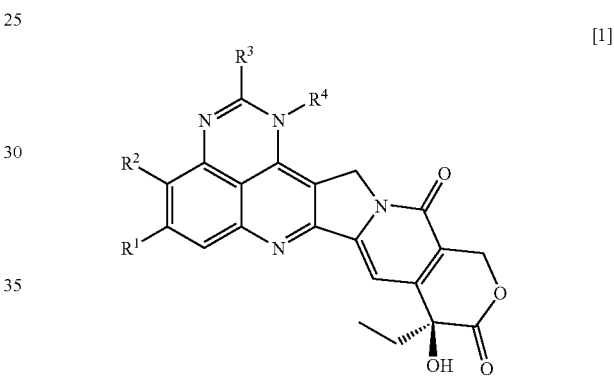

wherein

R$^1$ and R$^2$ are independently hydrogen, halogen, (C$_1$-C$_5$)-alkyl or (C$_1$-C$_5$)-alkoxy;

R$^3$ is hydrogen;

(C$_1$-C$_5$)-alkyl optionally substituted with one to three moieties independently selected from the group consisting of (C$_1$-C$_5$)-alkoxy, hydroxy, halogen, amino, (C$_3$-C$_7$)-cycloalkyl, heterocyclic ring and aryl in which the aryl ring is optionally substituted with one to three moieties independently selected from the group consisting of hydroxy, (C$_1$-C$_5$)-alkoxy, amino, mono-(C$_1$-C$_5$)-alkylamino or di-(C$_1$-C$_5$)-alkylamino;

R$^4$ is hydrogen;

(C$_1$-C$_{10}$)-alkyl, optionally substituted with one to three moieties independently selected from the group consisting of (C$_1$-C$_5$)-alkoxy, hydroxy, halogen, amino, mono-(C$_1$-C$_5$)-alkylamino, di-(C$_1$-C$_5$)-alkylamino and (C$_3$-C$_7$)-cycloalkyl, a heterocyclic ring and aryl in which the aryl ring is optionally substituted with one to three moieties independently selected from the group consisting of hydroxy, alkoxy, halogen, amino, mono-(C$_1$-C$_5$)-alkylamino and di-(C$_1$-C$_5$)-alkylamino;

or a pharmaceutically acceptable salt thereof, which comprises condensing a compound of the formula [2] or its salt,

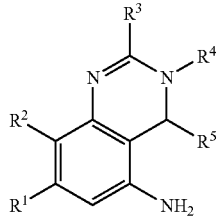

wherein $R^1$, $R^2$, $R^3$, $R^4$ are the same as defined above and $R^5$ is —OH or —O—$(C_1$-$C_5)$-alkyl, with a compound of formula [3],

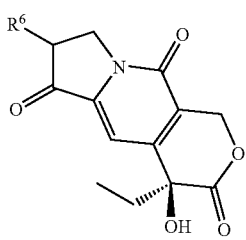

wherein $R^6$ is a chlorine or bromine.

2. The process according to claim 1 for the preparation of a compound of the formula [1] wherein $R^1$ and $R^2$ are independently hydrogen or $(C_1$-$C_3)$-alkyl;

$R^3$ is hydrogen;

$(C_1$-$C_5)$-alkyl optionally substituted with one to three moieties independently selected from the group consisting of $(C_1$-$C_5)$-alkoxy, hydroxy, halogen, amino, $(C_3$-$C_7)$ cycloalkyl, a heterocyclic ring and aryl in which the aryl ring is optionally substituted with one to three moieties independently selected from the group consisting of hydroxy, $(C_1$-$C_5)$-alkoxy and halogen;

$R^4$ is hydrogen;

$(C_1$-$C_8)$-alkyl which is optionally substituted with one to three moieties independently selected from the group consisting of $(C_1$-$C_3)$-alkoxy, hydroxy, halogen, amino, mono-$(C_1$-$C_3)$-alkylamino, di-$(C_1$-$C_3)$-alkylamino, $(C_3$-$C_7)$-cycloalkyl, a heterocyclic ring and aryl in which the aryl ring is optionally substituted with one to three moieties independently selected from the group consisting of hydroxy, $(C_1$-$C_5)$-alkoxy and halogen;

or a pharmaceutically acceptable salt thereof.

3. The process according to claim 1 for the preparation of a compound of the formula [1], or a pharmaceutically acceptable salt thereof, wherein $R^1$ and $R^2$ are hydrogen;

$R^3$ is hydrogen, methyl, ethyl, propyl, hydroxymethyl, aminomethyl, (methylamino)methyl, (dimethylamino)methyl, chloromethyl, or trifluoromethyl;

$R^4$ is methyl, ethyl, n-propyl, 1-methylethyl, n-butyl, 1,1-dimethylethyl, 2-methylpropyl, 2,2-dimethylpropyl, n-pentyl, 3-methylbutyl, 2-n-hexyl, 3,3-dimethylbutyl, n-heptyl, n-octyl, benzyl, phenethyl, 2-(dimethylamino) ethyl, 2-(4-morpholino)ethyl, 3-(dimethylamino)propyl, 2-(pyridin-2-yl)ethyl, 2-(pyridin-3-yl)ethyl, 2-(4-methoxyphenyl)ethyl, 2-(4-chlorophenyl)ethyl, 2-(4-fluorophenyl)ethyl, or 3-phenylpropyl.

4. The process according to claim 1 for the preparation of a compound of the formula [1A],

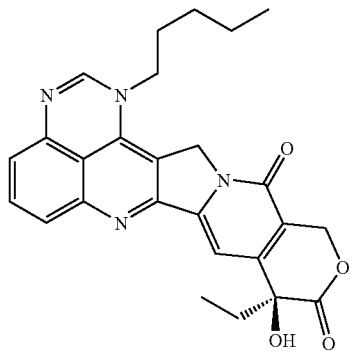

or a pharmaceutically acceptable salt thereof, which comprises condensing a compound of the formula [2A] or its salt,

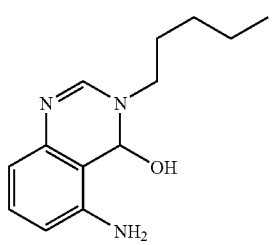

with a compound of the formula [3A],

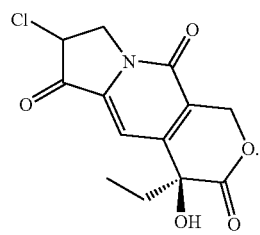

5. A process according to claim 1, wherein, before said condensing in claim 1, the process further comprises preparing said compound of formula [2] by a process comprising:

a) ozonolysis of a compound of the formula [4] or its salt,

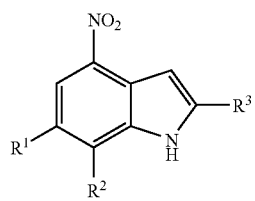

in order to obtain compound of the formula [5],

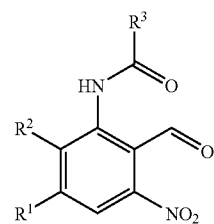

b) cyclizing the compound of the formula [5] with an amine $R^4$—$NH_2$ to obtain compound of the formula [6],

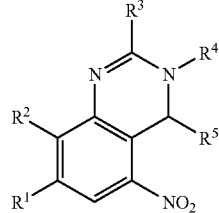

[6]

and c) hydrogenating the nitro group of a compound of the formula [6] in order to obtain the compound of the formula [2],

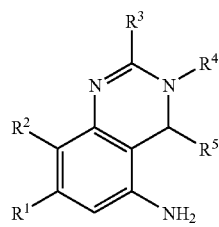

[2]

and before said condensing in claim 1, preparing said compound of formula [3] by a process comprising halogenating a compound of formula [8],

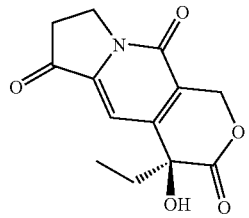

[8]

in order to obtain a compound of formula [3],

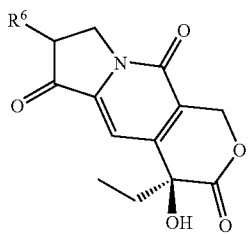

[3]

wherein:

$R^1$, $R^2$, $R^3$, $R^4$ and $R^5$ are as defined in claim 1, and $R^6$ is chlorine or bromine.

\* \* \* \* \*

UNITED STATES PATENT AND TRADEMARK OFFICE
CERTIFICATE OF CORRECTION

| | |
|---|---|
| PATENT NO. | : 7,595,400 B2 |
| APPLICATION NO. | : 10/546287 |
| DATED | : September 29, 2009 |
| INVENTOR(S) | : Fukuda et al. |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 655 days.

Delete the phrase "by 655 days" and insert -- by 863 days --

Signed and Sealed this

Eighteenth Day of May, 2010

David J. Kappos
*Director of the United States Patent and Trademark Office*